United States Patent [19]

Yamaoka et al.

[11] Patent Number: 5,023,327
[45] Date of Patent: Jun. 11, 1991

[54] FLUORINE-CONTAINING GLYCOSIDE AND ITS USE

[75] Inventors: Ryohei Yamaoka; Keizo Hayashiya; Tohru Yoshimura, all of Kyoto; Eiji Seki, Settsu; Tetsuya Masutani, Osaka; Katsuhiko Kitahara, Kyoto, all of Japan

[73] Assignee: Daikin Industries Ltd., Osaka, Japan

[21] Appl. No.: 315,535

[22] Filed: Feb. 27, 1989

[30] Foreign Application Priority Data

Feb. 27, 1988 [JP] Japan .................................. 63-46917

[51] Int. Cl.$^5$ ...................... C07H 15/04; A01N 43/18
[52] U.S. Cl. .................................. 536/18.4; 424/405; 424/DIG. 11
[58] Field of Search ....... 536/18.4; 424/405, DIG. 11

[56] References Cited

U.S. PATENT DOCUMENTS 4,582,901 4/1986 Prestwich .................... 424/DIG. 11
4,861,754 8/1989 Farkas-Himsley .................. 424/405
4,888,325 12/1989 Schroeder et al. ................. 424/405

FOREIGN PATENT DOCUMENTS 255443 2/1988 European Pat. Off. .
331089 9/1989 European Pat. Off. .

OTHER PUBLICATIONS

Metabolism of Tritiated w-Fluorofatty Acids and Alcohols in the Termite Reticulitermes Flavipes, by Glenn D. Prestwich, Ryohei Yamaoka and Joan F. Carvalho, Insect Biochemistry, 15 (2) (1984), pp. 205-209.

Isolation of 2-Fluorocitrate Produced by in Vivo Dealkylation of 29-Fluorostigmasterol in an Insect by Glenn D. Prestwich, Ryohei Yamaoka, Seloka Phirwa and Angelo DePalma, The Journal of Biological Chemistry, vol. 259, No. 17, Sep. 10, 1984, pp. 11022-11026.

Prestwich et al, Fluorolipids as Targeted Termiticides and Biochemical Probes, J. Agric. Food Chem., 1981, 29, pp. 1023-1027.

Primary Examiner—Ronald W. Griffin
Attorney, Agent, or Firm—Birch, Stewart, Kolasch & Birch

[57] ABSTRACT

An organism which generates energy through the decomposition of cellulose such as termites can be selectively destroyed with a fluorine-containing glycoside of the formula:

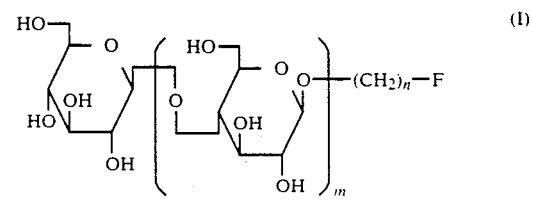

wherein n is an even number of 2 to 20, and m is an integer of 0 to 5.

9 Claims, No Drawings

FLUORINE-CONTAINING GLYCOSIDE AND ITS USE

BACKGROUND OF THE INVENTION

1. Field of the Invention

The present invention relates to a fluorine-containing glycoside and its use. More particularly, the present invention relates to a fluorine-containing glycoside, particularly ω-fluoroalkyl-β-cellobioside or glucoside and its use as well as an acyl derivative of the glycoside.

2. Description of the Related Art

In various places in the world, many wooden buildings have been built from ancient times to the present time. However, the wooden buildings suffer from significant damages caused by termites and wood rotting fungi.

Chlordan (1,2,3,4,5,6,7,8,8-octachloro-4,7-methano-3a,4,7,7a-tetrahydroindane) was widely used as a termiticide, but its use has been forbidden due to its residual toxicity and toxicity against other organisms.

Accordingly, it has been highly desirable to provide a new termiticide.

The termites can decompose, hardly decomposable cellulose with cellulase, to cellobiose and further decompose the cellibiose with cellobiase to glucose. Then, the glucose is introduced into the TCA cycle through glycolysis to obtain ATP. The enzymes, used in the above series of conversions are known as β-glucosidases, are specifically present in the termites, protozoas which are in commensal with the termites or the wood rotting fungi.

Meanwhile, an even number carbon alcohol having a fluorine at the ω-positioned, is oxidized to a corresponding fatty acid. Then, the fatty acid is decomposed with β-oxidation to a fluoroacetate and then converted to a fluorocitrate, which inhibits aconitase in the TCA cycle. Because of these mechanism, the ω-fluorinated even number carbon alcohol, is known to have 24 to 72 hour delayed toxicity (see Insect Biochemistry, 15 (2), 205-209, March, 1985.

The termites are known to exchange nutritions with other individuals, which is one of the characteristics of social insects. That is, foods once eaten by one individual can be distributed to other individuals in the forms of vomits and egesta from anus or in the form of secretions such as saliva. Then, the foods eaten by workers may be fed to the queen or king termites through several steps of nutrition exchange.

This indicates that, if the food had the delayed toxicity and eaten by individual termites, the toxic food could be propagated from one individual to other and finally spread throughout a whole colony of the termites.

Accordingly, if the ω-fluorinated alcohol were bonded to the cellulose, oligosaccharide, cellobiose or glucose throught the β-glycoside bond, it would be possible to provide a compound which has specific toxicity against the termites or the wood rotting fungi which generate energy through decomposition of cellulose with the β-glycosidase, while it has no toxicity against organisms which generate energy with α-glycosidase.

SUMMARY OF THE INVENTION

One object of the present invention is to provide a novel fluorine-containing glycoside.

Another object of the present invention is to provide a novel acyl derivative of a glycoside.

A further object of the present invention is to provide a method for destroying organisms which can generate energy through decomposition of cellulose with the β-glucosidase.

These and other objects of the present invention are accomplished by a fluorine-containing glycoside of the formula:

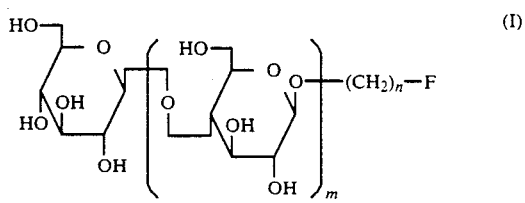
(I)

wherein n is an even number of 2 to 20, and m is an integer of 0 to 5.

DETAILED DESCRIPTION OF THE INVENTION

Among the compounds (I), those is which n is an even number of 12 to 18, particularly 16 to 18 preferred.

Specific examples of termites to be destroyed by the present invention are *Coptotermes formosanus Shiraki*, *Reticulitermes speratus Kolbe* and *Cryptotermes domesticus Haviland*.

The compound (I) may be prepared by reacting an acyl derivative of a glycoside of the formula:

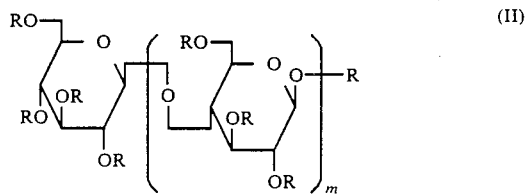
(II)

wherein R is an acyl group having 2 to 5 carbon atoms, and m are the same as defined above, which is obtainable by reacting cellobiose or glucose with a carboxylic acid or an acid anhydride of the formula:

ROH (III)

wherein R is the same as defined above or an anhydride thereof, with an ω-fluoroalcohol of the formula:

HO—(CH$_2$)$_n$—F (IV)

wherein n is the same as defined above.

The fluoroalcohol (IV) is a known compound and disclosed in, for example, Insect Biochemistry, loc. cit., the disclosure of which is incorporated by reference.

Although the ω-fluoroalcohol has toxicity against the organisms, its toxicity is not selective so that it is toxic against human beings and cattle. Therefore, the ω-fluoroalcohol as such cannot be used for destroying the termites or the wood rotting fungi. In addition, since the ω-fluoroalcohol has specific malodor, it is also repels the termites.

Acylation of the cellobiose, glucose or oligosaccharide with the carboxylic acid (III) or its anhydride as the acylating agent can be carried out in a suitable solvent at a temperature of from room temperature to a reflux temperature of the solvent in the presence of a base catalyst (e.g. trimethylamine and pyridine) in case of the acid anhydride or in the presence of a dehydration catalyst (e.g. dicyclohexyl carbodiimide and sulfuic acid) in case of the carboxylic acid. Preferred examples of the solvent are aromatic hydrocarbons such as benzene.

In the glycocylation of the acyl derivative (II) with the ω-fluoroalcohol (IV), equimolar amounts of these compounds and trimethylsilyl trifluoromethanesulfonate are treated in a suitable solvent in the presence of a molecular sieve as a catalyst. The reaction temperature is usually room temperature. The resulting compound of the formula:

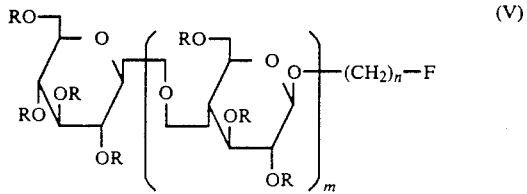
(V)

wherein R, n and m are the same as defined above is a novel compound and within the scope of the present invention.

The compound (V) is then deacylated according to a conventional method. For example, the compound (V) is deacylated with a solution of sodium methoxide in methanol usually at room temperature.

Since the fluoroalcohol (IV) is bonded to the saccharide residues in the compound (I) through the β-bonds, the compound (I) can be decomposed with the β-glucosidase which is specifically present in the termites and the wood rotting fungi to liberate the ω-alcohol (IV), which is toxic to destroy the termites and the wood rotting fungi. While, other organism, particularly mammals have α-glucosidase but no β-glucosidase, they cannot decompose the compound (I) so that no ω-fluoroalcohol is liberated from the compound (I) in the mammals. Accordingly, the compound (I) has selective toxicity against the termites and the wood rotting fungi.

When the compound (I) is used to destroying the termites or the wood rotting fungi, it is dissolved in a suitable solvent (e.g. methanol, ethanol, DMF, DIMSO, etc.) in a concentration of 10 to 50% by weight and carried on a suitable carrier such as a sheet of paper, wood chips, etc.

PREFERRED EMBODIMENTS OF THE INVENTION

The present invention will be illustrated further in detail by following examples.

EXAMPLE 1

A. ω-Fluorododecanol (405 mg, 1.9 mmol), cellobiose octacetate (2 g, 3.2 mmol) and trimethylsilyl trifluoromethanesulfonate (600 mg) were reacted in ethylene dichloride (20 ml) at 20° C. for about 3 hours in the presence of Molecular Sieve 4A powder as a catalyst.

After the reaction was terminated, the reaction mixture was washed with ether and filtered. The filtrate was washed with 1N sodium hydroxide and water successively and dried over anhydrous sodium sulfate.

B. ω-Fluorododecylheptacetylcellobioside obtained in the step A was subjected to silica gel chromatography and eluted with mixed solvents of hexane and ethyl acetate of a volume ratio of 70:30 and 50:50 (each 500 ml) and then with ether (500 ml). From the hexane/ethyl acetate (50:50) fraction, a mixture of α- and β-anomers was recovered. Then, the mixture was further subjected to the silica gel chromatography and eluted with the mixed solvent of hexane and ethyl acetate (50:50). The eluted fraction was evaporated to dryness to give the β-anomer (24 mg). Melting point: 161.5–162.5° C.

C. The β-anomer was dissolved in methanol and deacetylated with sodium methoxide at 25° C. to obtain ω-fluorododecyl-β-D-cellobioside (9 mg). This cellobioside was decomposed or carbonated at 156°–157° C.

The TMS derivative of this product silylated with BSTFA was subjected to the gas chromatography under the following conditions to give a single peak:

Gas Chromatography Conditions

Column: 3% OV-1, 1.5 m.
Injection temperature: 280° C.
Column temperature: 310° C.
Carrier gas: Nitrogen (20 ml/min.).

The β-anomer was used in the subsequent bioassay.

EXAMPLE 2

In the same manner as in Example 1 but using ω-fluorohexadecanol (40 mg) and cellobiose octacetate (250 mg), first ω-fluorohexadecyl-β-D-heptacetylcellobioside having a melting point of 117°–118.5° C. (250 mg) and then ω-fluorohexadecyl-β-D-cellobioside were prepared. This cellobioside was decomposed or carbonated at 215.5°–216° C.

EXPERIMENT 1

The bioassay was carried out with using 10 termite workers in a plastic dish containing wet sea sand for one series.

Before experiment, the termites fasted about one week to decoloring the wooden color from their abdomens.

The compounds to be tested were impregnated in Various concentrations into paper discs, which had been colored with mixture of food colors Green Blue No. 1 mixed with Yellow No. 4 (each 200 mg) dissolved in water (15 ml). The test compound was impregnated in the paper disc after diluting the solution with methanol, and after methanol was evaporated off, the paper disc was placed on the sea sand in the plastic dish. When the termites eat the test compound colored with the food colorants, they are colored green, which makes it easy to determine whether the termites eat the test compound or not.

After confirming the evaporation of methanol, the paper disc was placed in the plastic dish. To prevent the diffusion of the compound into the sand, a sheet of aluminum foil was placed between the paper disc and the sand.

Then, the plastic discs each containing the termites and the so-treated paper disc were placed in a thermostatic chamber kept at 25° C., and the condition of the termites was observed at the same time every day and water was supplied.

All the bioassay was conducted with three series for each test compound.

The results for ω-fluorododecyl-β-D-cellobioside (50 μg/paper disc) are shown in Table 1, in which "x/y" in the columns for the number of colored and dead termites and the total number of dead termites stands for (died on that day)/(total number of dead termites).

EXPERIMENT 2

In the same manner as in Example 1 but using ω-fluorohexadecyl-β-D-cellobioside of Example 2 (100 mg/dish) in place of ω-fluorododecyl-β-D-cellobioside, the bioassay was conducted. The results are shown in Table 2.

COMPARATIVE EXPERIMENT 1

In the same manner as in Experiment 1 but using ω-fluorododocanol (1 μg/dish) in place of ω-fluorododecyl-β-D-cellobioside, the bioassay was conducted. The results are shown in Table 3.

COMPARATIVE EXPERIMENT 2

In the same manner as in Experiment 1 but using ω-fluorohexadecanol (10 μg/paper disc) in place of ω-fluorododecyl-β-D-cellobioside, the bioassay was conducted. The results are shown in Table 4.

TABLE 1

| | | | | | | | | | | Days | | | | | | | | | | | |
|---|---|---|---|---|---|---|---|---|---|---|---|---|---|---|---|---|---|---|---|---|---|
| | | 1 | | 2 | | 3 | | 4 | 5 | | 6 | | 7 | | 8 | | 9 | | 10 | | 11 |
| Colored (%) | | | | | | | | | | | | | | | | | | | | | | |
| Series | 1 | 30 | 0 | 90 | 90 | 90 | 80 | 60 | 80 | 60 | 70 | 80 | 90 | 90 | 90 | 100 | 80 | 80 | 80 | 90 | 100 | 90 | 90 |
| | 2 | 0 | 22 | 22 | 0 | 75 | 75 | 75 | 75 | 75 | 75 | 75 | 71 | 71 | 71 | 71 | 71 | 71 | 71 | 71 | 71 | 85 | 71 |
| | 3 | 60 | 90 | 90 | 100 | 100 | 90 | 90 | 90 | 90 | 80 | 80 | 80 | 80 | 80 | 80 | 80 | 80 | 80 | 80 | 80 | 67 | 78 |
| Number of colored and dead termites | | | | | | | | | | | | | | | | | | | | | | | |
| Series | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 2 | 0 | 0 | 0 | 0 | 0 | 0 | 0 | 0 | 0 | 0 | 1 | 0 | 0 | 0 | 0 | 0 | 0 | 0 | 0 | 0 | 0 | 0 |
| | 3 | 0 | 0 | 0 | 0 | 0 | 0 | 0 | 0 | 0 | 0 | 0 | 0 | 0 | 0 | 0 | 0 | 0 | 0 | 0 | 1 | 0 | 0 |
| Total number of dead termites | | | | | | | | | | | | | | | | | | | | | | | |
| Series | 1 | 0 | 0 | 0 | 0 | 0 | 0 | 0 | 0 | 0 | 0 | 0 | 0 | 0 | 0 | 0 | 0 | 0 | 0 | 1 | 0 | 0 | 0 |
| | 2 | 1 | 0 | 0 | 1/2 | 0 | 0 | 0 | 0 | 0 | 0 | 1/3 | 0 | 0 | 0 | 0 | 0 | 0 | 0 | 0 | 0 | 0 | 0 |
| | 3 | 0 | 0 | 0 | 0 | 0 | 0 | 0 | 0 | 0 | 0 | 0 | 0 | 0 | 0 | 0 | 0 | 0 | 0 | 0 | 1 | 0 | 0 |

| | | | | | | | | Days | | | | | | | | | |
|---|---|---|---|---|---|---|---|---|---|---|---|---|---|---|---|---|---|
| | | 12 | | 13 | | 14 | | 15 | | 16 | 17 | 18 | | 19 | | | 20 |
| Colored (%) | | | | | | | | | | | | | | | | | | |
| Series | 1 | 90 | 100 | 100 | 100 | 100 | 100 | 100 | 100 | 100 | 100 | 100 | | | | | | |
| | 2 | 71 | 83 | 83 | 100 | 100 | 100 | 100 | 100 | 67 | 67 | 100 | 67 | 100 | 100 | | | |
| | 3 | 78 | 88 | 100 | 100 | 100 | 100 | 100 | 85 | 85 | 100 | 57 | 57 | 71 | 83 | 80 | | 100 |
| Number of colored and dead termites | | | | | | | | | | | | | | | | | | |
| Series | 1 | 0 | 1 | 0 | 3/4 | 0 | 2/6 | 1/7 | 0 | 0 | 1/8 | 1/9 | | | | | | |
| | 2 | 0 | 0 | 0 | 1/2 | 0 | 0 | 1/3 | 0 | 0 | 0 | 0 | 0 | 2/5 | 0 | 1/6 | | |
| | 3 | 0 | 0 | 0 | 0 | 1/2 | 0 | 0 | 0 | 0 | 0 | 0 | 0 | 1/3 | 0 | 2/5 | | 3/8 |
| Total number of dead termites | | | | | | | | | | | | | | | | | | |
| Series | 1 | 0 | 1/2 | 0 | 3/5 | 0 | 2/7 | 1/8 | 0 | 0 | 1/9 | 1/10 | | | | | | |
| | 2 | 0 | 1/4 | 1/5 | 1/6 | 0 | 0 | 1/7 | 0 | 0 | 0 | 0 | 0 | 2/9 | 0 | 1/10 | | |
| | 3 | 0 | 1/2 | 0 | 0 | 1/3 | 0 | 0 | 0 | 0 | 0 | 0 | 0 | 0 | 1/4 | 3/7 | | 3/10 |

TABLE 2

| | | | | | | | | | | Days | | | | | | | | |
|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 |
| Colored (%) | | | | | | | | | | | | | | | | | | | |
| Series | 1 | 0 | 75 | 45 | 65 | 55 | 30 | 35 | 30 | 0 | 30 | 0 | 0 | 0 | 65 | 60 | 50 | 100 | |
| | 2 | 0 | 60 | 30 | 75 | 75 | 75 | 75 | 75 | 50 | 35 | 25 | 65 | 65 | 40 | 60 | 65 | 80 | 100 |
| | 3 | 0 | 100 | 75 | 75 | 65 | 45 | 65 | 45 | 20 | 0 | | | | | | | | |
| Total number of dead termites | | | | | | | | | | | | | | | | | | | |
| Series | 1 | 1 | | | | | 2 | 3 | 4 | | | | | | 5 | 8 | 9 | 10 | |
| | 2 | | | 1 | 2 | | 3 | | | | 4 | | | | | 4 | 5 | 8 | 10 |
| | 3 | 1 | | | | | 2 | 3 | 4 | 8 | 10 | | | | | | | | |

TABLE 3

| | | | | Days | | | |
|---|---|---|---|---|---|---|---|
| | | 1 | 2 | 3 | 4 | 5 | 6 |
| Colored (%) | | | | | | | |
| Series | 1 | 0 | | 100 | 100 | 100 | 100 |
| | 2 | 0 | | | | | |
| Total number of dead termites | | | | | | | |
| Series | 1 | | 7 | 9 | | | 10 |
| | 2 | | 4 | 7 | 10 | | |

TABLE 4

| | Time (hrs) | | | | | | | | | |
|---|---|---|---|---|---|---|---|---|---|---|
| | 12 | 24 | 36 | 48 | 60 | 72 | 84 | 96 | 120 | 132 |
| Number of Colored termites | | | | | | | | | | |
| Series 1 | 0 | 0 | 7 | 9 | 9 | | | | | |
| 2 | 0 | 10 | 10 | 10 | 8 | | | | | |
| 3 | 9 | 9 | 7 | 10 | 9 | | | | | |
| Number of dead termites | | | | | | | | | | |
| Series 1 | 0 | 0 | 0 | 0 | 5/5 | 1/6 | 0/6 | 4/10 | | |
| 2 | 0 | 0 | 0 | 2 | 5/7 | 3/10 | | | | |
| 3 | 0 | 0 | 0 | 1 | 1/2 | 4/6 | 1/7 | 0/7 | 1/8 | 2/10 |
| Number of colored and dead termites | | | | | | | | | | |
| Series 1 | 0 | 0 | 0 | 0 | 5 | 1 | 0 | 4 | | |
| 2 | 0 | 0 | 0 | 2 | 5 | 2 | | | | |
| 3 | 0 | 0 | 0 | 1 | 1 | 4 | 1 | 0 | 1 | 2 |

What is claimed is:

1. A fluorine-containing glycoside of the formula:

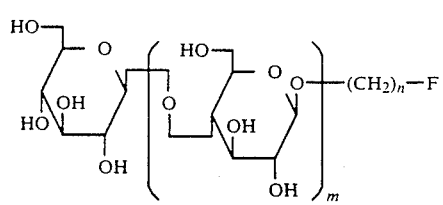

(I)

wherein n is an even number of 2 to 20, and m is an integer of 0 to 5.

2. The fluorine-containing glycoside according to claim 1, wherein n is an even number of 12 to 20.

3. The fluorine-containing glycoside according to claim 2, wherein n is 16 or 18.

4. An acylated derivative of a glycoside of the formula:

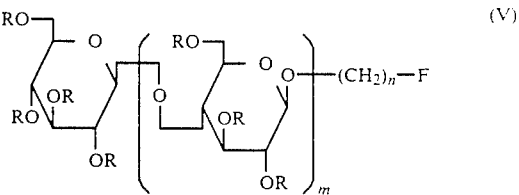

(V)

wherein R is an acyl group having 2 to 5 carbon atoms, n is an even number of 2 to 2Q, and m is an integer of 0 to 5.

5. The acylated derivative of the glycoside according to claim 4, wherein n is an even number of 12 to 20.

6. A method for destroying an organism which generates energy through decomposition of cellulose, which method comprises feeding a fluorine-containing glycoside of the formula:

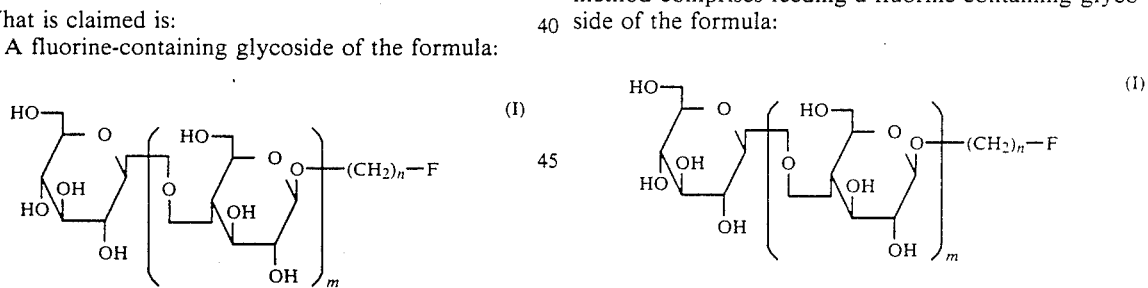

(I)

wherein n is an even number of 2 to 20, and m is an integer of 0 to 5 to the organism.

7. The method according to claim 6, wherein n in the formula (I) is an even number of 12 to 20.

8. The method according to claim 7, wherein n is 16 or 18.

9. The method according to claim 6, wherein the organism to be destroyed is termites.

* * * * *